(12) United States Patent
Wu et al.

(10) Patent No.: US 10,108,845 B2
(45) Date of Patent: Oct. 23, 2018

(54) ANOMALY DETECTION FOR MEDICAL SAMPLES UNDER MULTIPLE SETTINGS

(71) Applicant: Hong Kong Applied Science and Technology Research Institute Company Limited, Hong Kong (HK)

(72) Inventors: Xiaohua Wu, Hong Kong (HK); Yan Nei Law, Hong Kong (HK)

(73) Assignee: Hong Kong Applied Science and Technology Research Institute Company Limited, Hong Kong (HK)

( * ) Notice: Subject to any disclaimer, the term of this patent is extended or adjusted under 35 U.S.C. 154(b) by 132 days.

(21) Appl. No.: 15/447,315

(22) Filed: Mar. 2, 2017

(65) Prior Publication Data

US 2018/0253589 A1 Sep. 6, 2018

(51) Int. Cl.
*G06K 9/00* (2006.01)
*G06K 9/62* (2006.01)
(Continued)

(52) U.S. Cl.
CPC ......... *G06K 9/00147* (2013.01); *G01N 21/64* (2013.01); *G01N 33/483* (2013.01);
(Continued)

(58) Field of Classification Search
CPC ............. G06K 9/00147; G06K 9/3241; G06K 9/00134; G06K 9/0014; G06K 9/4652;
(Continued)

(56) References Cited

U.S. PATENT DOCUMENTS 7,899,514 B1    3/2011 Kirkland et al.
8,718,377 B2 *  5/2014 Suzuki .................. G06T 7/0012
                                                  382/128

(Continued)

FOREIGN PATENT DOCUMENTS

WO    2016087592 A1    6/2016
WO    2016115280 A1    7/2016

OTHER PUBLICATIONS

International Search Report and Written Opinion of PCT application No. PCT/CN2017/075587 issued from the International Search Authority dated Dec. 13, 2017.
Jeannette Chang, Pablo Arbeláez, Neil Switz, Clay Reber, Asa Tapley, J. Lucian Davis, Adithya Cattamanchi, Daniel Fletcher, and Jitendra Malik, "Automated Tuberculosis Diagnosis Using Fluorescence Images from a Mobile Microscope," Med Image Comput Comput Assist Interv. 2012; 15(Pt 3): 345-352.

(Continued)

*Primary Examiner* — Tom Y Lu
(74) *Attorney, Agent, or Firm* — Spruson & Ferguson (Hong Kong) Limited (57) ABSTRACT

Using multiple imaging modes in whole slide image screening is potentially useful to reduce false positives. To use multiple imaging modes, a method for locating anomalies on a medical sample from an image thereof uses an anomaly-detection process that comprises using plural base classifiers individually to classify an object-of-interest suspected to be an anomaly. Each base classifier respectively extracts features of the object-of-interest and generates, according to the extracted features, a score indicating a likelihood of the object-of-interest being anomalous. The anomaly-detection process further comprises using an aggregate classifier to combine the scores generated by the base classifiers to determine whether the object-of-interest is the anomaly. The aggregate classifier determines a dependability measure for each base classifier according to setting-based variables of a setting under which the sample and the image are obtained, and then selectively combines the scores of the base classifiers according to the dependability measures.

20 Claims, 3 Drawing Sheets

(51) Int. Cl.
G06K 9/46 (2006.01)
G06T 7/00 (2017.01)
G06K 9/32 (2006.01)
G01N 33/483 (2006.01)
G01N 21/64 (2006.01)

(52) U.S. Cl.
CPC ....... *G06K 9/0014* (2013.01); *G06K 9/00134* (2013.01); *G06K 9/3241* (2013.01); *G06K 9/4647* (2013.01); *G06K 9/4652* (2013.01); *G06K 9/623* (2013.01); *G06K 9/6269* (2013.01); *G06K 9/6277* (2013.01); *G06K 9/6282* (2013.01); *G06T 7/0014* (2013.01); *G06K 2209/05* (2013.01); *G06T 2207/10024* (2013.01); *G06T 2207/10056* (2013.01); *G06T 2207/10064* (2013.01); *G06T 2207/30024* (2013.01)

(58) Field of Classification Search
CPC .. G06K 9/6269; G06K 9/4647; G06K 9/6282; G06K 9/623; G06K 9/6277; G06K 2209/05; G06T 7/0014; G06T 2207/10064; G06T 2207/10024; G06T 2207/3002; G01N 33/483; G01N 21/64
See application file for complete search history.

(56) References Cited

U.S. PATENT DOCUMENTS

| | | |
|---|---|---|
| 2013/0156305 A1 | 6/2013 | Prasad et al. |
| 2014/0064581 A1* | 3/2014 | Madabhushi ........ G06K 9/6256 382/128 |
| 2014/0233826 A1 | 8/2014 | Agaian et al. |
| 2014/0314286 A1* | 10/2014 | Madabhushi ......... G06T 7/0012 382/128 |
| 2015/0110381 A1* | 4/2015 | Parvin ................. G06K 9/6249 382/133 |
| 2015/0227809 A1 | 8/2015 | Alpert et al. |
| 2016/0042511 A1 | 2/2016 | Chukka et al. |
| 2016/0110584 A1* | 4/2016 | Remiszewski ........ G06T 7/0012 382/133 |
| 2017/0193078 A1* | 7/2017 | Limonad ........... G06F 17/30572 |
| 2018/0007074 A1* | 1/2018 | Kune ........................ G06F 1/28 |

OTHER PUBLICATIONS

Corina Pangilinan, Ajay Divekar, Gerrit Coetzee, Dave A. Clark, Bernard Fourie, Fleming Y. M. Lure, and Sean Kennedy, "Application of Stepwise Binary Decision Classification for Reduction of False Positives in Tuberculosis Detection From Smeared Slides," Proceedings of the IASTED International Symposia, Imaging and Signal Processing in Healthcare and Technology (ISPHT 2011), May 16-18, 2011, Washington DC, USA.

* cited by examiner

ANOMALY DETECTION FOR MEDICAL SAMPLES UNDER MULTIPLE SETTINGS

FIELD OF THE INVENTION

The present invention relates to anomaly detection for a medical sample in computer aided diagnosis (CAD).

BACKGROUND

Anomaly detection is crucial for CAD. Whole slide image (WSI) searching is preferred for CAD to avoid false negatives but is limited by its image acquisition and processing speed. Most of the existing approaches for WSI screening use low-magnification images in order to reduce image acquisition time. Thus, image quality becomes degraded. Information contained in low-magnification images is less than that in high-resolution ones, thus imposing limitations in accurately segmenting and classifying anomalies. Moreover, large searching area in WSI screening introduces more false positives, which affect diagnostic results as well.

Using multiple imaging modes in WSI screening is potentially useful to reduce false positives. At present, most products do not provide WSI analysis for evaluation and do not support multiple imaging modes. They only use samples from a single setting (e.g., same exposure time, same experiment) for classification. Besides, most of them are machine dependent, which are not easy to be adapted to new hardware settings.

Typically, two imaging modes are used in current products for image analysis: the fluorescence (FL) mode and the brightfield (BF) mode. However, both modes have their own shortcomings. For the FL mode, despite a relatively high sensitivity among different imaging modes, objects other than anomalies often emit green fluorescence as well under excitation. It may cause false positive results, thereby affecting accuracy of diagnostic results. For the BF mode, which results in a low contrast when compared to the FL mode, calibration is required due to color variation of dye in samples from different experiments.

Thus, there is a need in the art for a technique that supports multiple imaging modes and makes use of multi-mode results in enhancing accuracy in anomaly detection. The technique is especially useful in anomaly detection for WSIs.

SUMMARY OF THE INVENTION

A first aspect of the present invention is to provide a computer-implemented method for locating one or more anomalies on a medical sample from an image thereof. The medical simple and the image are prepared under a setting comprising one or more setting-based variables. In the method, any object-of-interest suspected to be anomalous on the medical sample are identified and located from the image. When one or more objects-of-interest are located, whether an individual object-of-interest is an individual anomaly is determined by an anomaly-detection process. The anomaly-detection process is repeated for each of the one or more objects-of-interest. The anomaly-detection process comprises using plural base classifiers individually to classify the individual object-of-interest. Each base classifier respectively extracts features of the individual object-of-interest and generates, according to the extracted features, a score indicating a likelihood of the individual object-of-interest being anomalous. The anomaly-detection process further comprises using an aggregate classifier to combine the scores generated by the base classifiers to determine whether the individual object-of-interest is the individual anomaly. The aggregate classifier determines a dependability measure of an individual score for each base classifier according to the one or more setting-based variables, and selectively combines the scores of all the base classifiers according to the dependability measures of the scores.

The image may be obtained by imaging an entire slide on which the medical sample resides for carrying out WSI screening of the one or more anomalies. The image may be a brightfield image or a fluorescent image.

The base classifiers are usually selected according to practical applications. In one choice, a first base classifier is arranged to extract morphological features of the individual object-of-interest, and to use one or more decision trees to classify the morphological features for generating the score. In another choice, a second base classifier is arranged to extract local histogram features of the individual object-of-interest, and to use a support vector machine to classify the local histogram features for generating the score. When the image is a color image, one or more color histograms are used for extracting the local histogram features. When the image is a grayscale image, one or more intensity histograms are used for extracting the local histogram features. In yet another choice, a third base classifier is a convolutional neural network.

A second aspect of the present invention is to provide a multistage method for detecting one or more targeted anomalies having a pre-selected characteristic on a medical sample. The method comprises at least a first stage and a second stage. In the first stage, a first staining agent is applied to the medical sample for staining anomalies including the one or more targeted anomalies. After the anomalies are stained, the medical sample is imaged to give a first image. One or more computers then locate the anomalies from the first image by a locating process according to one or more first setting-based variables of a first setting under which the medical sample and the first image are obtained. In particular, the locating process is arranged according to any embodiment provided by the first aspect of the present invention. In the second stage, a second staining agent is applied to the medical sample for re-staining the one or more targeted anomalies. The second staining agent is formulated to preferentially stain a subset of the anomalies where the anomalies in the subset have the pre-selected characteristic. After the one or more targeted anomalies are re-stained, the medical sample is imaged to give a second image. Optionally, the second image is obtained by imaging the medical sample only on areas surrounding the anomalies that are located front the first image. Thereafter, the one or more computers locate the one or more targeted anomalies from the second image by the locating process according to one or more second setting-based variables of a second setting under which the medical sample and the second image are obtained. The one or more targeted anomalies are thereby detected.

Other aspects of the present invention are disclosed as illustrated by the embodiments hereinafter.

DETAILED DESCRIPTION

The present invention addresses the need for a technique that supports multiple imaging modes in detecting anomalies on a medical sample and makes use of resultant multiple detection results to enhance accuracy in detecting the anomalies. In addition, the present invention is particularly useful for WSI screening by improving detection accuracy while still allowing the use of low-magnification images in the detection. WSI screening means that an entire slide on which a medical sample resides is imaged to give an image and the image is analyzed for anomaly detection. Nonetheless, the application of the present invention is not limited only to WSI screening.

The Inventors have observed that different classifiers have different performances on medical samples prepared under different experimental conditions and imaged for analysis under different imaging conditions. Usually, one classifier has performance in anomaly detection better than another classifier for a medical sample and an image thereof obtained under a certain setting, where the aforesaid setting is a combination of the experimental conditions and the imaging conditions. It follows that it is advantageous to incorporate different classifiers into a detector for detecting anomalies and then intelligently combines the results of different classifiers according to side information provided by the setting used to obtain the medical sample and the image thereof. By such combination, the confidence level or accuracy in anomaly detection can be enhanced. The present invention is developed based on the aforementioned observation.

A first aspect of the present invention is to provide a computer-implemented method for locating one or more anomalies on a medical sample from an image thereof. The medical sample and the image are prepared under a setting.

More particularly, the setting comprises one or more setting-based variables, where the one or more setting-based variables are used to model or characterize the setting. The one or more setting-based variables form a collection of the experimental conditions and the imaging conditions respectively used in obtaining the medical sample and the image thereof. Examples of an individual setting-based variable include a type of the image (e.g., a BE image or a FL image), an exposure time in imaging the medical sample, a staining agent applied to the medical sample for staining anomalies thereon, whether the medical sample under consideration is one of samples obtained from a particular experiment, etc.

Figure 1:
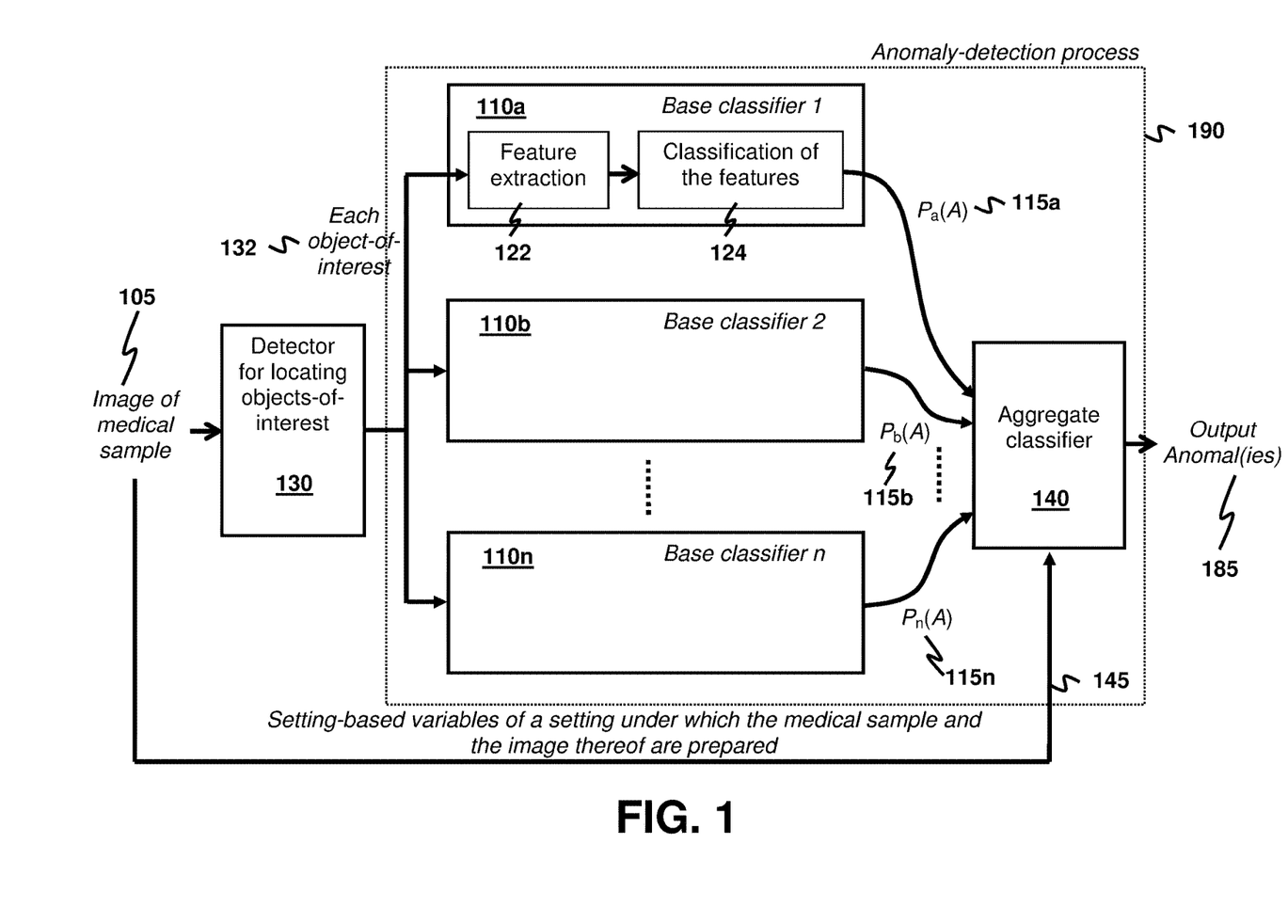
FIG. 1 depicts a processing flow of detecting one or more anomalies from an image of a medical sample in accordance with an exemplary embodiment of the present invention, where the one or more anomalies are detected by plural base classifiers and an aggregate classifier.

The method is exemplarily illustrated with an aid of FIG. 1. FIG. 1 depicts a processing flow of detecting one or more anomalies 185 from an image 105 of a medical sample in accordance with an exemplary embodiment of the present invention.

The image 105 is first processed by a location detector 130 to detect and locate any object-of-interest suspected to be anomalous on the medical sample. As an initial step, it is desired to include as many possible anomalies as possible in order to keep the chance of missing any anomaly low. Usually and desirably, the location detector 130 is programmed to identify and locate the suspected anomalies efficiently and in a short time. Those skilled in the art will appreciate that various algorithms in the art can be used to achieve such quick detection. For example, candidate objects-of-interest may be located by using morphological operations and template matching as taught by J. Chang et al., "Automated Tuberculosis Diagnosis Using Fluorescence Images from a Mobile Microscope," *Med Image Compul Comput Assist Intern.*, 2012,15(Pt 3), pp. 345-352. After one or more objects-of-interest are located, these suspected anomalies are then scrutinized to determine the ones that are genuine anomalies, and to reject those that are not in order to eliminate false positives or reduce them as many as possible. In particular, when one or more objects-of-interest are detected and located by the location detector 130, an anomaly-detection process 190 is performed to determine whether an individual object-of-interest 132 is an individual anomaly. The anomaly-detection process 190 is repeated for all the identified one or more objects-of-interest to yield one or more anomalies 185 with locations thereof provided by the location detector 130, or no anomaly if not detected.

The anomaly-detection process 190 is detailed as follows.

Plural base classifiers 110a-110n are individually used to classify the individual object-of-interest 132. That is, each of the base classifiers 110a-110n is independently used to classify the individual object-of-interest 132. Structures of the base classifiers 110a-110n are similar. Without loss of generality, consider the base classifier 110a for illustration. The base classifier 110a extracts features of the individual object-of-interest 132 (as shown in block 122) and generates a score 115a, denoted as $P_a(A)$, indicating a likelihood of the individual object-of-interest 132 being anomalous (as shown in block 124). Hence, the base classifiers 110a-110n respectively yield the scores 115a-115n denoted as $P_a(A)$, $P_b(A)$, ..., $P_n(A)$.

Although FIG. 1 depicts a total of 14 base classifiers, 110a-110n, for illustration, the present invention is not limited only to this number of base classifiers. The base classifiers 110a-110n used in the anomaly-detection process 190 and the number of them are usually selected according to practical applications. In the art, many machine learning-based classifiers can be used to realize the base classifiers 110a-110n, e.g., the classifiers that score or grade objects for screening anomalies in medical-sample images as suggested in US2014/0233826, US2016/0042511 and WO2016/087592 as well as in the following references, the disclosures of which are incorporated by reference herein: J. Chang et al., "Automated Tuberculosis Diagnosis Using Fluorescence Images from a Mobile Microscope," *Med Image Comput Commit Assist Interv.*, 2012, 15(Pt 3), pp. 345-352; and C. Pangilinan et al., "APPLICATION OF STEPWISE BINARY DECISION CLASSIFICATION FOR REDUCTION OF FALSE POSITIVES IN TUBERCULOSIS DETECTION FROM SMEARED SLIDES," *Proceedings of the IASTED International Symposia, imaging and Signal Processing in Healthcare and Technology (ISPHT 2011)*, May 16-18, 2011. As a non-limiting example for illustration, consider an application of detecting tuberculosis (TB). The disclosed method is adapted for the medical sample suspected to contain one or more types of acid-fast bacilli (AFB). In this application, two base classifiers 110a, 110b are used. The base classifier 110a is arranged or programmed to extract morphological features of the individual object-of-interest 132, and to use one or more decision trees to classify the morphological features for generating the score $P_a(A)$ 115a. The base classifier 110b is arranged or programmed to extract local histogram features of the individual object-of-interest 132, and to use a support vector machine (SVM) to classify the local histogram features for generating the score $P_b(A)$ 115*b*. If the image 105 is a color image, one or more color histograms are used for extracting the local histogram features. If, on the other hand, the image 105 is a grayscale image, one or more intensity histograms are used for extracting the local histogram features. Instead of using the local histogram features for classification, alternatively the base classifier 110*b* may be realized as a convolutional neural network (CNN).

After the scores 115*a*-115*n* are generated by the base classifiers 110*a*-110*n*, an aggregate classifier 140 is used to combine the scores 115*a*-115*n* to determine whether the individual object-of-interest 132 is the individual anomaly. In particular, the aggregate classifier 140 takes the scores 115*a*-115*n* of the base classifiers 110*a*-110*n* as well as one or more setting-based variables 145 to learn a model for an improved decision. The one or more setting-based variables 145 are parameters of a setting under which the medical sample and the image thereof 105 are obtained. One method that the aggregate classifier 140 combines the scores 115*a*-115*n* is provided as follows. The aggregate classifier 140 first determines a dependability measure of the score that is generated by each of the base classifiers 110*a*-110*n* according to the one or more setting-based variables 145. The dependability measure of an individual score is a degree of belief, or trust, that the score is correct. In particular, the dependability measure is determined according to the one or more setting-based variables 145. For example, if, based on theoretical analysis or observed through previous experimental findings, the base classifier 110*a* is known unlikely to be accurate when a particular setting-based variable falls within a certain range of values, then the dependability measure of the individual score is given a low value. In the special case that the classifier 110*a* is known to be inaccurate under such particular setting-based variable, the dependability measure may be given a value of zero. If the dependability measure of a certain score is lower than a pre-determined threshold value, the score is preferred to be dropped and not taken into consideration in determining whether the individual object-of-interest 132 is anomalous. If the dependability measure of the score is greater than the pre-determined threshold value, it is preferred to include the score in the determination of whether the individual object-of-interest 132 is an anomaly. Finally, the aggregate classifier 140 selectively combines the scores 115*a*-115*n* according to the dependability measures thereof.

The selective combination of the scores 115*a*-115*n* may be realized in different ways. In a first realization, the scores having their dependability measures greater than the pre-determined threshold values are selected and the remaining scores are dropped. The selected scores are averaged, and the resultant average score is used to determine whether the individual object-of-interest 132 is anomalous. For instance, if the resultant average score is greater than a second pre-determined threshold value, then the individual object-of-interest 132 is determined to be an anomaly. In a second realization, the score having the highest dependability measure among all the scores 115*a*-115*n* is selected. If the selected score is greater than the second pre-determined threshold value, the individual object-of-interest 132 is determined to be an anomaly. In a third realization, the selection of the scores is the same as that of the first realization. A median of the selected scores is then computed, and the median score is used to determine whether the individual object-of-interest 132 is anomalous. The aforementioned three realizations are not exhaustive and serve only as embodiments.

Figure 2:
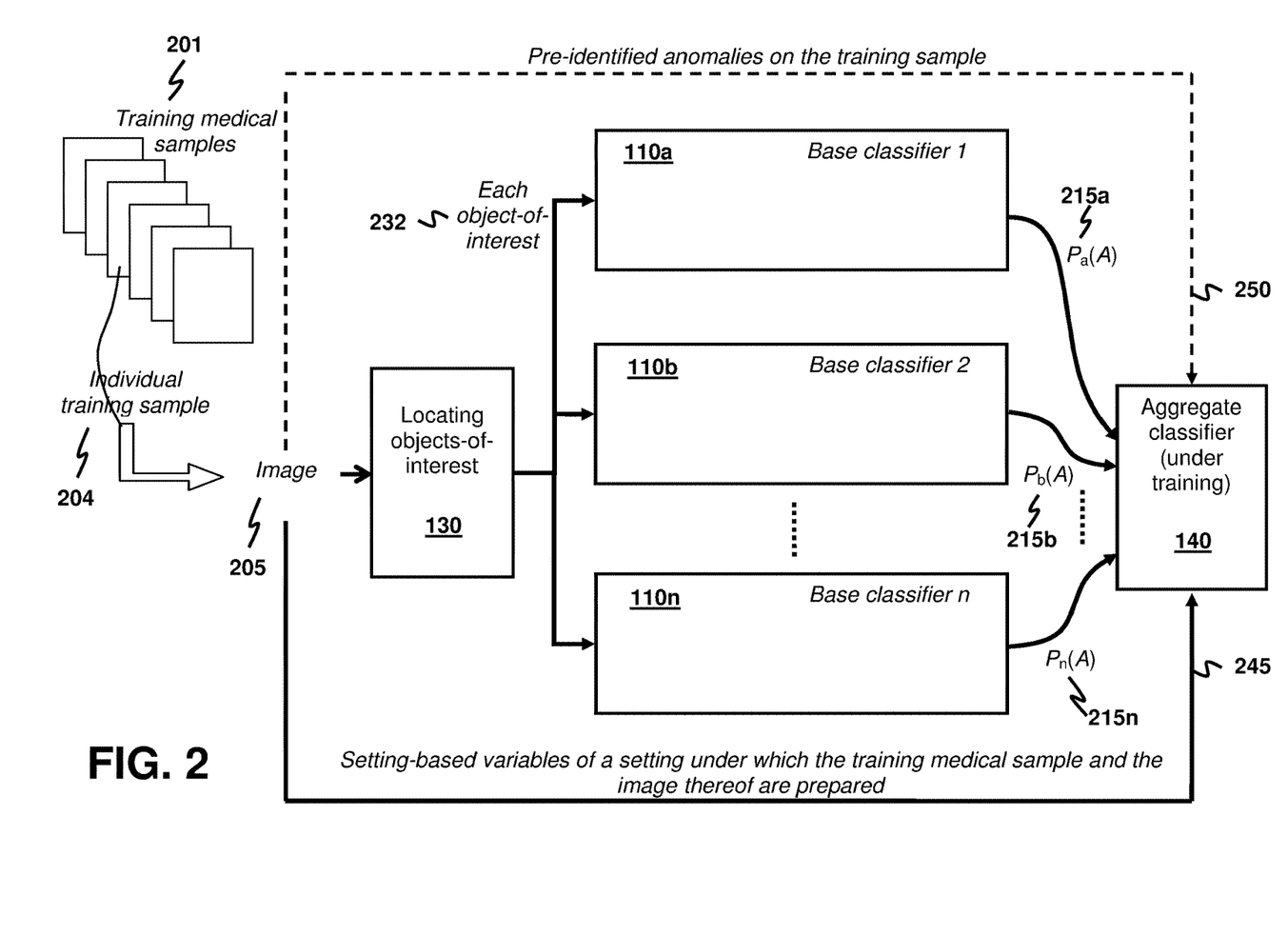
FIG. 2 depicts an exemplary arrangement of training the base classifiers and the aggregate classifier of FIG. 1.

Generally, the base classifiers 110*a*-110*n* and the aggregate classifier 140 are machine learning-based algorithms that require training prior to execution of the anomaly-detection process 190. An exemplary arrangement of training is depicted in FIG. 2. The base classifiers 110*a*-110*n* and the aggregate classifier 140 are trained by images of plural training medical samples 201, each of the training medical samples 201 having pre-identified one or more anomalies. In addition, an individual training sample 204 and its image 205 are obtained under a pre-selected setting. For the individual training sample 204, objects-of-interest thereof suspected to be anomalies are first located by the location detector 130 from an image 205 of the individual training sample 204. An individual object-of-interest 232 is processed by the base classifiers 110*a*-110*n*, resulting in a plurality of scores 215*a*-215*n*. The aggregate classifier 140 is then trained with the plurality of scores 215*a*-215*n* as inputs. The aggregate classifier 140 is supplied with a list 250 of the pre-identified one or more anomalies. It follows that the aggregate classifier 140 has a knowledge of whether the individual object-of-interest 232 under consideration is an anomaly or not. The aggregate classifier 140 also receives setting-based variables 245 of the aforesaid setting associated with the individual training sample 204. The scores 215*a*-215*n* are checked with the aforementioned knowledge to assess quality of classifier outputs for all the base classifiers 110*a*-110*n* under the setting-based variables 245 used in obtaining the individual training sample 204 and the image thereof 205. Thereby, the aggregate classifier 140 is trained. As will soon become evident, it is preferred to train the base classifiers 110*a*-110*n* and the aggregate classifier 140 with different settings for most practical applications.

As a remark, the aggregate classifier 140 is different from the teaching of WO2016/087592 in the following aspect. In WO2016/087592, a statistical model is used to combine different scores into a single final score according to some model parameters. An example of the statistical model is a Cox model. During training, individual scores due to classifying a training sample of a patient and the survival outcome data of the patient are used to estimate the model parameters of the Cox model. In a non-training session of analyzing a medical sample under test, the model parameters used by the statistical model in combining individual scores of the medical sample are unrelated to the medical sample under test. That is, the model parameters are invariant to the medical sample under test. On the other hand, the aggregate classifier 140 in the non-training session receives the one or more setting-based variables 145 that are related to the medical sample and the image thereof 105. The one or more setting-based variables 145 are directly used to determine the dependability measures of the scores 115*a*-115*n*, where the dependability measures are used in the selective combination of the scores 115*a*-115*n*. Hence, the dependability measures depend on the medical sample under test.

A second aspect of the present invention is to provide a multistage method for detecting one or more targeted anomalies having a pre-selected characteristic on a medical sample. The method comprises at least a first stage and a second stage. In each stage, an embodiment of the computer-implemented method for the first aspect is used.

Figure 3:
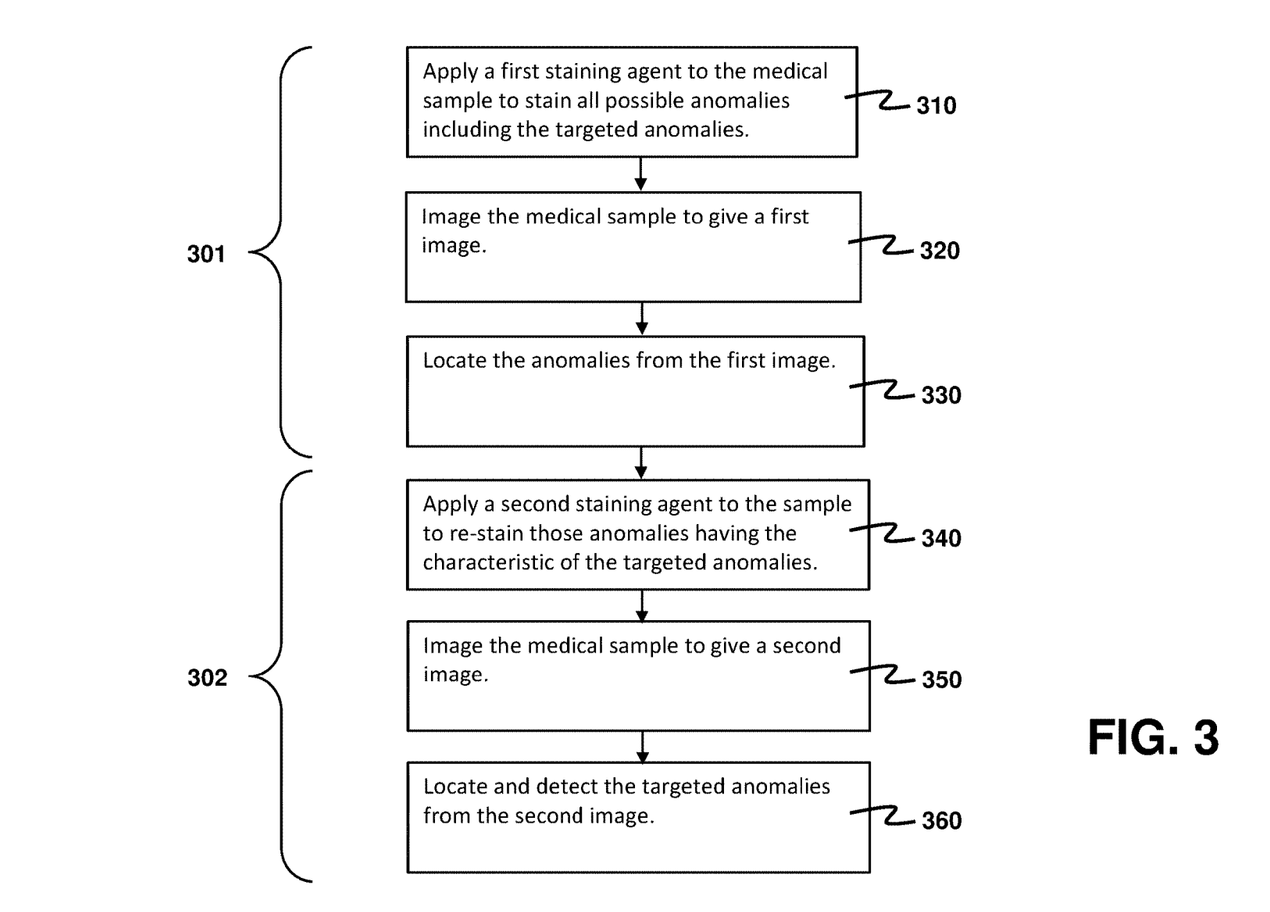
FIG. 3 depicts a flowchart for illustrating a multistage method for detecting one or more targeted anomalies having a pre-selected characteristic where each stage is implemented with the processing flow of FIG. 1.

FIG. 3 depicts a flowchart illustrating the steps of the multistage method according to one embodiment of the present invention. The method includes a first stage 301 and a second stage 302. The first stage 301 is aimed at identifying and locating as many anomalies on the medical sample as possible. These anomalies include the one or more targeted anomalies. After these anomalies are identified, the second stage 302 is to examine these anomalies one by one in order to identify the one or more targeted anomalies from the anomalies identified in the first stage 301. The first stage 301 comprises steps 310, 320 and 330. The second stage 302 includes steps 340, 350 and 360.

In describing the method as follows, occasionally an application of the method for detecting TB is used as an illustrative example. For TB detection, the one or more targeted anomalies are AFB, and the pre-selected characteristic is the presence of large amounts of mycolic acids within cell walls of AFB.

In the first stage 301, a first staining agent is applied to the medical sample for staining anomalies including the one or more targeted anomalies in the step 310. Usually, the medical sample is put on a slide for easy handling. One choice of the first staining agent is a high-sensitivity staining agent such as Acridine Orange (AO), which is a diary methane dye often used as a fluorescent stain. The high-sensitivity staining agent enables a very high percentage of the anomalies to be revealed so as to be subsequently detected.

After the anomalies are stained, the medical sample on the slide is scanned and imaged to give a first (digital) image in the step 320. Preferably, a WSI is employed to enable all the anomalies on the medical sample to be detected in subsequent steps. AO is a nucleic acid-selective fluorescent cationic dye useful for cell cycle determination. Therefore, if the first staining agent is AO, the first image is obtained under the FL mode.

One or more computers are then used in the step 330 to locate the anomalies from the first image by a locating process. The locating process is arranged or programmed according to any embodiment of the anomaly-locating method as disclosed in the first aspect of the present invention. Given that the medical sample and the first image are obtained under a first setting comprising one or more first setting-based variables, the locating process determines the anomalies according to the one or more first setting-based variables. If AO is used as the first staining agent, the one or more first setting-based variables may include a first item indicating that the medical sample is stained with AO, and a second item indicating that the FL mode is used in obtaining the first image. At the end of the first stage 301, the anomalies including the one or more targeted anomalies are identified and located.

In the second stage 302, a second staining agent is applied to the medical sample for re-staining the one or more targeted anomalies in the step 340. The second staining agent is formulated to preferentially stain a subset of the anomalies where the anomalies in the subset have the pre-selected characteristic. If it is desired to determine whether the medical sample contains TB pathogens, one suitable choice of the second staining agent is a high-specificity staining agent such as Ziehl-Neelsen (ZN) stain or acid-fast stain. The ZN stain is a special bacteriological stain used to identify AFB for image processing under the BF mode.

After the one or more targeted anomalies are re-stained, the medical sample on the slide is scanned or imaged to give a second image in the step 350. A WSI may be used to scan the slide. Alternatively, it is also possible to scan only areas surrounding the anomalies that are already located in the step 320 since the second stage 302 is focused on examining the anomalies identified in the first stage 301. Using this option saves some scanning time. If the ZN stain is used as the second staining agent, the second image is obtained under the BF mode.

The one or more computers are then used in the step 360 to locate the one or more targeted anomalies from the second image by the locating process according to one or more second setting-based variables of a second setting under which the medical sample and the second image are obtained. If the ZN stain is used as the second staining agent, the one or more second setting--based variables may include one item indicating that the medical sample is stained with the ZN stain, and another item indicating that the BF mode is used in obtaining the second image. At the end of the second stage 302, the one or more targeted anomalies are detected.

Using the disclosed method for TB detection provides the following advantages. The first stage 301 is adapted to detect as many anomalies including AFB as possible by using a high-sensitivity staining agent. The first stage 301 is intended to minimize misses in identifying genuine AFB to offset a higher likelihood of miss induced by using a low-magnification first image instead of a high-resolution one. However, the use of the high-sensitivity staining agent increases a likelihood of including false positives (i.e. anomalies that are not AFB). The likelihood of getting false positives is further increased if WSis are used. In the second stage 302, the anomalies identified in the first stage 301 are re-stained with a high-specificity staining agent to reveal genuine AFB. Its purpose is to identify the false positives as many as possible and eliminate them from the anomalies identified in the first stage 301. Hence, the disclosed method enables TB detection using low-magnification images with a high detection probability through minimizing the misses while false positives are reduced as many as possible.

Those skilled in the art will appreciate that one or more additional stages may be added to the multistage method according to above-disclosed teachings about the first stage 301 and the second stage 302.

The present invention may be embodied in other specific forms without departing from the spirit or essential characteristics thereof. The present embodiment is therefore to be considered in all respects as illustrative and not restrictive. The scope of the invention is indicated by the appended claims rather than by the foregoing description, and all changes that come within the meaning and range of equivalency of the claims are therefore intended to be embraced therein.

What is claimed is:

1. A computer-implemented method for locating one or more anomalies on a medical sample from an image thereof, the medical sample and the image being prepared under a setting comprising one or more setting-based variables, the method comprising:

locating, from the image, any object-of-interest suspected to be anomalous on the medical sample; and when one or more objects-of-interest are located, determining whether an individual object-of-interest is an individual anomaly by an anomaly-detection process and repeating the anomaly-detection process for each of the one or more objects-of-interest;

wherein the anomaly-detection process comprises:

using plural base classifiers individually to classify the individual object-of-interest, wherein each base classifier respectively extracts features of the individual object-of-interest and generates, according to the extracted features, a score indicating a likelihood of the individual object-of-interest being anomalous; and using an aggregate classifier to combine the scores generated by the base classifiers to determine whether the individual object-of-interest is the individual anomaly, wherein the aggregate classifier determines a dependability measure of an individual score for each base classifier according to the one or more setting-based variables, and selectively combines the scores of all the base classifiers according to the dependability measures of the scores.

2. The method of claim 1, wherein the image is obtained by imaging an entire slide on which the medical sample resides.

3. The method of claim 1, wherein one of the base classifiers is arranged to extract morphological features of the individual object-of-interest, and to use one or more decision trees to classify the morphological features for generating the score.

4. The method of claim 1, wherein one of the base classifiers is arranged to extract local histogram features of the individual object-of-interest, and to use a support vector machine (SVM) to classify the local histogram features for generating the score.

5. The method of claim 4, wherein when the image is a color image, one or more color histograms are used for extracting the local histogram features.

6. The method of claim 4, wherein when the image is a grayscale image, one or more intensity histograms are used for extracting the local histogram features.

7. The method of claim 1, wherein one of the base classifiers is a convolutional neural network (CNN).

8. The method of claim 1, wherein:
the base classifiers include a first base classifier and a second base classifier;
the first classifier is arranged to extract morphological features of the individual object-of-interest, and to use one or more decision trees to classify the morphological features for generating the score; and
the second classifier is arranged to extract local histogram features of the individual object-of-interest, and to use a support vector machine (SVM) to classify the local histogram features for generating the score.

9. The method of claim 1, wherein:
the base classifiers include a first base classifier and a second base classifier;
the first classifier is arranged to extract morphological features of the individual object-of-interest, and to use one or more decision trees to classify the morphological features for generating the score; and
the second classifier is a convolutional neural network (CNN).

10. The method of claim 1, wherein the image is a brightfield image.

11. The method of claim 1, wherein the image is a fluorescent image.

12. The method of claim 1, wherein the one or more setting-based variables include a type of the image, the type of the image being selected front a brightfield image and a fluorescent image.

13. The method of claim 12, wherein the one or more setting-based variables further include art exposure time in imaging the medical sample.

14. The method of claim 1, wherein the one or more setting-based variables include a staining agent applied to the medical sample for staining the one or more anomalies before the medical sample is imaged.

15. The method of claim 1, further comprising:
before the anomaly-detection process is performed, training the base classifiers and the aggregate classifier with images of plural training medical samples each having pre--identified one or more anomalies, wherein an individual training medical sample and the image thereof are obtained under a pre-selected setting.

16. The method of claim 1, wherein the method is adapted for the medical sample suspected to contain one or more types of acid-fast bacilli (AFB).

17. A method for detecting one or more targeted anomalies having a pre-selected characteristic on a medical sample, comprising:
applying a first staining agent to the medical sample for staining anomalies including the one or more targeted anomalies;
after the anomalies are stained, imaging the medical sample to give a first image;
locating, by one or more computers, the anomalies from the first image by a locating process according to one or more first setting-based variables of a first setting under which the medical sample and the first image are obtained, wherein the locating process is arranged according to the method of claim 1;
applying a second staining agent to the medical sample for re-staining the one or more targeted anomalies, wherein the second staining agent is formulated to preferentially stain a subset of the anomalies where the anomalies in the subset have the pre-selected characteristic;
after the one or more targeted anomalies are re-stained, imaging the medical sample to give a second image; and
locating, by the one or more computers, the one or more targeted anomalies from the second image by the locating process according to one or more second setting-based variables of a second setting under which the medical sample and the second image are obtained, whereby the one or more targeted anomalies are detected.

18. The method of claim 17, wherein after the one or more targeted anomalies are re-stained, the medical sample is imaged only on areas surrounding the anomalies that are located from the first image.

19. A method for detecting one or more targeted anomalies having a pre-selected characteristic on a medical sample, comprising:
applying a first staining agent to the medical sample for staining anomalies including the one or more targeted anomalies;
after the anomalies are stained, imaging the medical sample to give a first image;
locating, by one or more computers, the anomalies from the first image by a locating process according to one or more first setting-based variables of a first setting under which the medical sample and the first image are obtained, wherein the locating process is arranged according to the method of claim 8;
applying a second staining agent to the medical sample for re-staining the one or more targeted anomalies, wherein the second staining agent is formulated to preferentially stain a subset of the anomalies where the anomalies in the subset have the pre-selected characteristic;
after the one or more targeted anomalies are re-stained, imaging the medical sample to give a second image; and
locating, by the one or more computers, the one or more targeted anomalies from the second image by the locating process according to one or more second setting-based variables of a second setting under which the medical sample and the second image are obtained, whereby the one or more targeted anomalies are detected.

20. A method for detecting one or more targeted anomalies having a pre-selected characteristic on a medical sample, comprising:

applying a first staining agent to the medical sample for staining anomalies including the one or more targeted anomalies;

after the anomalies are stained, imaging the medical sample to give a first image;

locating, by one or more computers, the anomalies from the first image by a locating process according to one or more first setting-based variables of a first setting under which the medical sample and the first image are obtained, wherein the locating process is arranged according to the method of claim 9;

applying a second staining agent to the medical sample for re-staining the one or more targeted anomalies, wherein the second staining agent is formulated to preferentially stain a subset of the anomalies where the anomalies in the subset have the pre-selected characteristic;

after the one or more targeted anomalies are re-stained, imaging the medical sample to give a second image; and locating, by the one or more computers, the one or more targeted anomalies from the second image by the locating process according to one or more second setting-based variables of a second setting under which the medical sample and the second image are obtained, whereby the one or more targeted anomalies are detected.

\* \* \* \* \*